(12) United States Patent
Haber et al.

(10) Patent No.: US 6,576,789 B1
(45) Date of Patent: Jun. 10, 2003

(54) PROCESS FOR THE PREPARATION OF SUBSTITUTED PHENYLBORONIC ACIDS

(75) Inventors: Steffen Haber, Landau/Pfalz (DE); Andreas Meudt, Floersheim-Weilbach (DE); Stefan Scherer, Buettelborn (DE); Frank Vollmueller, Mainz (DE)

(73) Assignee: Clariant GmbH, Frankfurt (DE)

( * ) Notice: Subject to any disclaimer, the term of this patent is extended or adjusted under 35 U.S.C. 154(b) by 0 days.

(21) Appl. No.: 09/553,036

(22) Filed: Apr. 20, 2000

(30) Foreign Application Priority Data

Apr. 21, 1999 (DE) .......................... 199 17 979

(51) Int. Cl.$^7$ ............................. C07F 5/02; C07F 5/04
(52) U.S. Cl. .......................................... 562/7; 558/287
(58) Field of Search ............................ 562/7; 558/384, 558/286, 287; 556/402

(56) References Cited

U.S. PATENT DOCUMENTS

| | | | |
|---|---|---|---|
| 3,038,926 A | * | 6/1962 | Farthouat |
| 5,631,364 A | | 5/1997 | Sundrehagen et al. |
| 6,117,372 A | | 9/2000 | Bogdanovic et al. |
| 6,296,788 B1 | | 10/2001 | Giffels et al. |

FOREIGN PATENT DOCUMENTS

| | | | |
|---|---|---|---|
| DE | 199 33 833 | | 1/2001 |
| EP | 757982 | * | 2/1997 |
| EP | 0 790 234 | | 8/1997 |
| GB | 984 363 | | 2/1965 |
| WO | WO 98/02443 | | 1/1998 |

OTHER PUBLICATIONS

CA:123:24519 abs of Chem Mater by Aleandri et al 7(6) pp 1153–70, 1995.*
CA:109:5481 abs of Acc Chem Res by Bogdanovic et al 21(7) pp 261–7, 1988.*
CA:103:6382 abs of J Chem Soc Chem Commun byRaston et al (24) pp 1702–3, 1984.*
CA:109:37850 abs of J Org Chem by Harvey et al 53(14) pp 3134–40, 1988.*
CA:113:132257 abs of Chem Ber by Feulner et al 123(9) pp 1841–43, 1990.*
N. Miyaura, et al. Palladium–Catalyzed Cross–Coupling Reactions of Organoboron Compounds, Chem. Rev. 1995, 95, 2457–2483.
H. Jendralla, et al., Efficient, Simple Procedures for the Large–Scale Preparation of Building Blocks for Angiotensin (II) Receptor Antagonists, Liebigs Ann. 1995, 1253–1257.
Derwent Patent Family Abstract for WO 98/02443 1/98.
D. E. Pearson, et al., A Study of the Entrainment Method for Making Grignard Reagents, J. Org Chem 1959, 24, 504–509.
T. Fife, et al., Oxazolidine Hydrolysis. The Participation of Solvent and Buffer in Ring Opening, J. Am. Chem. Soc. 1968, 1007–1014.
D. Witiak, et al., Peri Fluoro Steric Effects: Syntheses and Comparative Acid–Catalyzed Isomerization of the 8–, 9–, and 11–Fluoro–1,2,3,4–tetrahydro–7,12–dimethylbenz[a] anthracenes to Exo Methylene Tautomers, J. Org. Chem. 1988, 53, 345–352.
Y. Ito, et al., A New Approach to Asymmetric Synthesis of Polycycles on the Basis if o–Quinodimethane Generation, J. Am Chem Soc. 1983, 105, 1586–1590.
Derwent Patent Family Abstract for EP 0 790 234 8/97.
D. Ginsberg, The Action of t–Butyl Hypochlorite on Organic Compounds. II. Aromatic Aldehydes, J. Amer. Chem. Soc. 1951, 73, 702–704.
M. V. Sargent, Naturally Occurring Dibenzofurans. Part 9.$^1$ A Convenient Synthesis of Phthalide: The Synthesis of Methyl Di–O methylporphyrilate, J. Chem. Soc. 1987, Perkin Trans 1, (1), 231–235.

(List continued on next page.)

Primary Examiner—Jean F. Vollano
(74) Attorney, Agent, or Firm—Scott E. Hanf

(57) ABSTRACT

Compounds of the formula (I)

$$\text{(I)}$$

in which

Q$^1$ and Q$^2$ are each OH or form a trimeric boric anhydride, Z is CHO, CH$_2$Y, X or a protected aldehyde group, and X is CN, COOH, COCl, CONH$_2$ or C(OR)$_3$, and Y is OH or NH$_2$, and Z is in the o-, m- or p-position to the boronic acid radical, are prepared by a) reacting a compound of the formula (II)

$$\text{(II)}$$

with Mg in the presence of an anthracene compound and, if desired, a transition-metal halide and, if desired, an Mg halide or in the presence of a transition-metal halide and, if desired, an Mg halide, to give the corresponding arylmagnesium chloride, b) reacting the latter with a borate of the formula B(OR')$_3$ and hydrolyzing the product, with removal of the aldehyde protecting group, c) and, if desired, oxidizing or reducing the free aldehyde group.

10 Claims, No Drawings

OTHER PUBLICATIONS

K.T. Liu, et al., Catalytic Hydration of Nitriles to Amides with Manganese Dioxide on Silica Gel, Synthesis 1988 (9), 715–717.

P.R. Hamann, et al., The Efficient Synthesis of Two Prostraglandin Intermediates, Synthetic Communications, 1989, 19(9&10), 1509–1518.

Shoppe: Symmetrical Triad Prototropic Systems, J. Chemical Society, 1933, IX, p. 43.

B.S. Biggs, et al., "Decamethylenediamine", Organic Synthesis, 1947, 27, pp. 18–20.

Y.–H Lai, "Grignard reagents from chemically active magnesium", Synthesis, 1981, pp. 585–604.

XP–002199198, H. Feulner, et al., "Darstellung und strukturelle charakterisierung der p–formylbenzoboronsaure", Chemische Berichte, 123, 1990, pp. 1841–1843—See CF Below for translation.

H. Feulner, et al., "Preparation and structural characterization of p–formylbenzene–boronic acid", Beitrage zur Chemie des Bors, 206, 6 pages (1990).

* cited by examiner

PROCESS FOR THE PREPARATION OF SUBSTITUTED PHENYLBORONIC ACIDS

CROSS-REFERENCES TO RELATED APPLICATIONS

The present invention is described in the German priority application No. DE 199 17 979.4, filed Apr. 21, 1999, which is hereby incorporated by reference as is fully disclosed herein.

BACKGROUND OF THE INVENTION

Substituted phenylboronic acids, for example cyanophenylboronic acids, are of considerable industrial importance as precursors for active compounds, in particular as precursors for correspondingly substituted biphenyl derivatives, which are used as AT(II) antagonists, or as precursors for liquid-crystalline compounds, as liquid crystals or as a constituent of liquid-crystalline mixtures. Phenylboronic acids can be coupled to haloaromatic compounds with transition-metal catalysis to give biphenyl derivatives with the aid of methods described in the literature (N. Miyaura et al., Tetrahedron Lett., 3437 (1979); A. L. Casalnuovo et al., J. Amer. Chem. Soc. 112, 4324 (1990), N. Miyaura et al., Chem. Rev. 95 (1995), 2457–2483).

The conventional synthetic routes for cyanophenylboronic acids, either starting from carboxyphenylboronic acid via the formation of the acid amide with subsequent formation of the cyano compound or starting from the correspondingly substituted bromobenzonitrile by reaction with organolithium compounds, such as butyllithium, followed by reaction with a trialkyl borate, do not achieve the object of an economical synthesis of cyanophenylboronic acids which is simple to carry out industrially, since firstly the synthetic route contains too many steps, and secondly, organolithium compounds are very expensive and hazardous to handle.

The Grignard reaction with chlorobenzaldehyde proceeds in low yields and very slowly, meaning that for industrial purposes, it was hitherto necessary to use expensive bromobenzaldehyde (H. Jendralla et al., Liebigs Ann. 1995, 1253–1257).

WO 98/02 443 uses transition-metal compounds, if necessary in combination with co-catalysts, for activating aromatic chlorine compounds for Grignard reactions, but not for chlorinated aromatic aldehydes or protected derivatives thereof. Rather, it is known that ether and acetal protecting groups considerably reduce the reactivity of the magnesium by forming complexes at the magnesium surface (D. E. Pearson et al., J. Org. Chem., 1959, 24, 504–509).

SUMMARY OF THE INVENTION

Owing to the interest in this class of substances, there is a need for an economical synthesis of substituted phenylboronic acids, in particular of cyanophenylboronic acids, which is simple to carry out industrially.

DESCRIPTION OF THE PREFERRED EMBODIMENTS

This object is achieved by a process for the preparation of a compound of the formula (I)

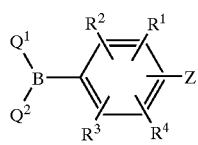

(I)

in which $Q_1$ and $Q^2$ are each OH or together are a divalent radical of the formula (Ib)

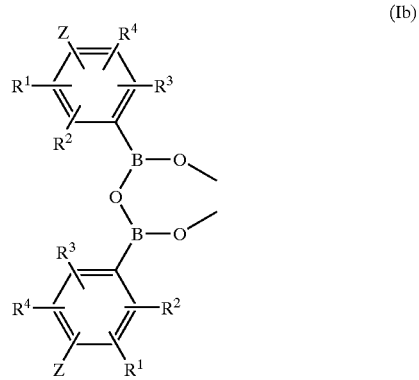

(Ib)

Z is —CHO, D, —CH$_2$Y or X, where D is a protected aldehyde group, Y is hydroxyl or amino, and X is cyano, COOH, COCl, CONH$_2$ or C(OR)$_3$, where R is C$_1$–C$_5$-alkyl or phenyl, and where Z is in the ortho-, meta- or para-position to the boronic acid radical;

R$^1$ to R$^4$, independently of one another, are hydrogen, C$_1$–C$_{12}$-alkyl, C$_2$–C$_{12}$-alkenyl, C$_2$–C$_{12}$-alkynyl, C$_3$–C$_{12}$-cycloalkyl, (C$_1$–C$_{12}$-)-alkoxy, O-phenyl, O-benzyl, aryl, heteroaryl, fluorine, N(alkyl)$_2$, N[Si (C$_1$–C$_4$-alkyl)$_3$]$_2$ or CF$_3$, or R$^1$ and R$^2$, and/or R$^3$ and R$^4$, together form a 5- or 6-membered aliphatic or aromatic ring; which comprises a) reacting a compound of the formula (II)

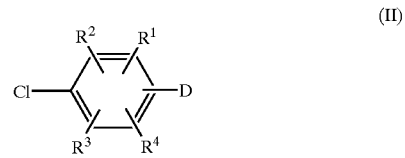

(II)

with magnesium in the presence of i) an anthracene compound and, if desired, a transition-metal halide and, if desired, a magnesium halide; or ii) a transition-metal halide and, if desired, a magnesium halide, where the anthracene compound is a compound from the group consisting of anthracene, Mg anthracene, substituted anthracene and substituted Mg anthracene, to give an arylmagnesium chloride of the formula (III)

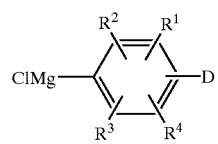

(III)

b) reacting the compound of the formula (III) with a borate of the formula B(OR')$_3$, in which R' are identical to or different from one another and are straight-chain or branched (C$_1$–C$_8$)-alkyl radicals, phenyl radicals which are unsubstituted or substituted by one or two (C$_1$–C$_4$)-alkyl groups or (C$_1$–C$_4$)-alkoxy groups, in particular straight-chain or branched (C$_1$–C$_4$)-alkyl radicals or unsubstituted phenyl radicals, and hydrolyzing the product to give a compound of the formula (IV)

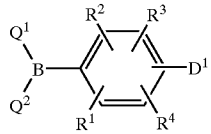

(IV)

in which

D$^1$ is CHO or D;

Q$^1$ and Q$^2$ are each OH or together are a divalent radical of the formula (IVb)

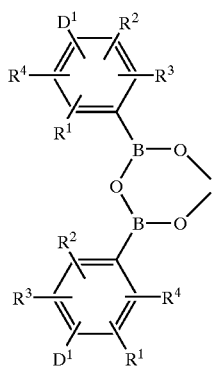

(IVb)

c) if desired oxidizing the compound of the formula (IV) or (IVb) in which D$^1$ is CHO to give a compound of the formula (I) in which Z is X, or if desired reducing the compound of the formula (IV) or (IVb) to give a compound of the formula (I) in which Z is CH$_2$Y.

In the above definitions, alkyl is preferably C$_1$–C$_4$-alkyl, aryl is preferably phenyl, alkylaryl is preferably benzyl, and alkoxy is preferably C$_1$–C$_4$-alkoxy.

Preferred radicals R (Z is —C(OR)$_3$) are C$_1$–C$_4$-alkyl, in particular methyl, ethyl or phenyl.

Preferred radicals R$^1$ to R$^4$ are hydrogen, methyl, ethyl, propyl, butyl, methoxy, ethoxy, propoxy, butoxy and fluorine.

The radical D is preferably an acetal of the formula (V) or (VI)

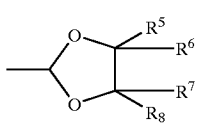

(V)

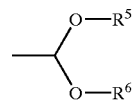

(VI)

in which R$^5$ to R$^8$ are identical or different and are hydrogen, C$_1$–C$_{12}$-alkyl or phenyl, or R$^6$ and R$^7$ together form a 5- or 6-membered aliphatic or aromatic ring; or D is an oxazolidine of the formula (VII) or an oxazoline of the formula (VIII)

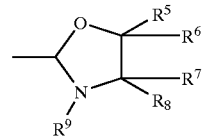

(VII)

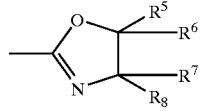

(VIII)

in which R$^5$ to R$^8$ are as defined above, and R$^9$ is C$_1$–C$_6$-alkyl, phenyl or benzyl, unsubstituted or substituted on the aromatic ring.

It was surprising that compounds of the formula (I) can be prepared in good yields by the process according to the invention starting from ortho-, meta- or para-chlorobenzaldehyde,.

Preferred borates B(OR')$_3$ are trimethyl borate, triethyl borate, tri-n-propyl borate, triisopropyl borate, tri-n-butyl borate and triisobutyl borate.

The group D is, if desired, converted into a compound of the formula (I) in which Z is —CHO by acidic hydrolysis or (in the case of the oxazolines) by reduction followed by acidic hydrolysis. It is also possible to remove the aldehyde protecting group in a one-pot process and, without prior isolation of a compound of the formula (IV) in which D$^1$ is D, to obtain a compound of the formula (IV) in which D$^1$ is —CHO.

It is likewise possible, by reacting compounds of the formula (IV) with alcohols of the formula HO-(C$_1$–C$_{12}$)-alkyl, HO-(C$_2$–C$_{12}$)-alkenyl, HO-(C$_2$–C$_{12}$)-alkynyl, HO-aryl or HO-alkylaryl, to prepare acyclic boronates of the formula (IVa)

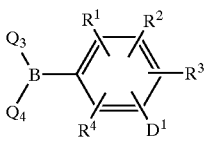

(IVa)

in which Q$^3$ and Q$^4$ are a radical of said alcohols, or, by reaction with the polyhydric alcohols (C$_3$–C$_{12}$)-cycloalkane-1,2-diol, (C$_5$–C$_{12}$)-cycloalkene-1,2-diol, (C$_5$–C$_{12}$)-cycloalkane-1,3-diol, (C$_5$–C$_{12}$)-cycloalkene-1,3-diol or with the alcohols of the formulae (1) to (6)

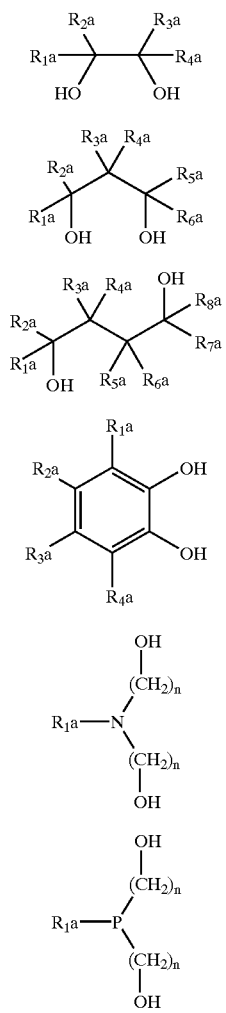

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, ($C_1$–$C_{12}$)-alkoxy, O-phenyl, O-benzyl, aryl, heteroaryl, fluorine, chlorine, $NH_2$, NH(alkyl), N(alkyl)$_2$, N[Si($C_1$–$C_4$-alkyl)$_3$]$_2$ or $CF_3$, and/or two adjacent radicals $R_1a$ to $R_8a$ together form a 5- or 6-membered aliphatic or aromatic ring, and in which n is an integer from 2 to 12, to prepare a cyclic borate of the formula (IVa) in which $Q^3$ and $Q^4$ together are a divalent radical of said polyhydric alcohols.

The compounds of the formula (IVa) can be converted back into compounds of the formula (IV) by acidic hydrolysis.

The compounds of the formula (I) in which Z is CHO, X or —$CH_2Y$ can likewise be converted into the compounds of the formula (Ia) by reaction with the above-mentioned alcohols.

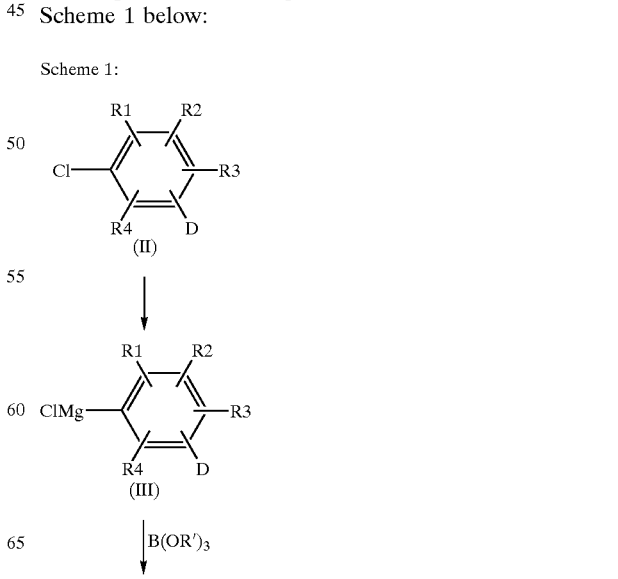

The compounds of the formula (Ia) can be converted back into compounds of the formula (I) by acidic hydrolysis.

The reaction of the compound of the formula (I) or of the formula (IV) with the alcohols on which the radicals $Q^3$ and $Q^4$ are based is advantageously carried out in the presence of an organic solvent which is inert toward the reaction participants, such as tetrahydrofuran, methyl tert-butyl ether, toluene, o-, m- or p-xylene, hexane or heptane, at a temperature of from 20° C. to the boiling point of the solvent used. In the case of diols or other polyhydric alcohols, it is also possible to use methanol, ethanol, n- or isopropanol as inert solvent. The diol on which the radicals $Q^3$ and $Q^4$ are based is advantageously employed in an equimolar amount, based on the boronic acid.

Preferred radicals $Q^3$ and $Q^4$ are —O-($C_1$–$C_6$)alkyl, —O-($C_2$–$C_6$)alkenyl, —O-($C_3$–$C_6$)-alkynyl, —O-phenyl, —O-benzyl, or $Q^3$ and $Q^4$, together with the boron atom, form a cyclic boronate with the alcohols ethylene glycol, 1,2-propanediol, 1,3-propanediol, 1,4-butanediol, 2,2-dimethylpropane-1,3-diol, pyrocatechol, pinacol, 2,3-dihydroxynaphthalene, 1,2-dihydroxycyclohexane, 1,3-dihydroxycyclopentane or 1,2-dihydroxycyclooctane.

Particularly preferred radicals $Q^3$ and $Q^4$, together with the boron atom, form a cyclic boronate with the alcohols ethylene glycol, 1,3-propanediol, 2,2-dimethyl-1,3-diol, pinacol and pyrocatechol.

The trimeric compounds of the formula (Ib) or (IVb) can be prepared from the corresponding monomeric compounds of the formula (I) or (IV) respectively, for example by heating at from 40 to 100° C., preferably from 50 to 75° C.

The process according to the invention is shown in Scheme 1 below:

Scheme 1:

-continued

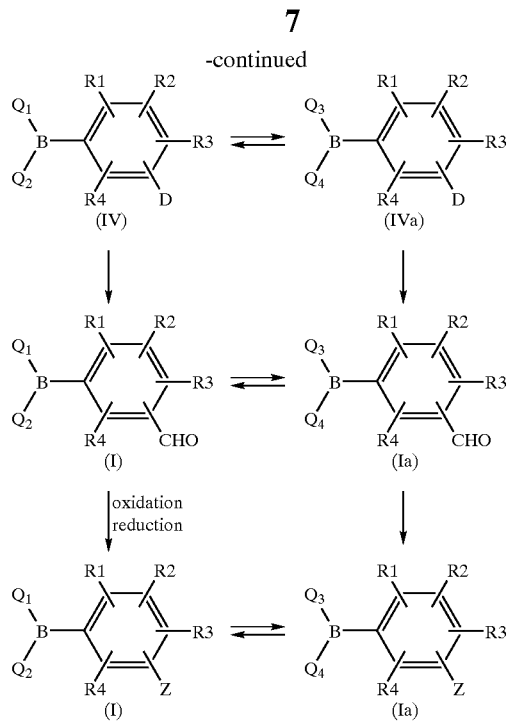

The aldehyde group is firstly converted into a magnesium-unreactive form, for example into a cyclic or a cyclic acetal, preferably ethylene glycol acetal, dimethyl or diethyl acetal, an oxazolidine or an oxazoline.

Chlorobenzaldehydes can be reacted with 1,2-diols by conventional methods to give correspondingly substituted 1,3-dioxolanes of the general formula (V) or with trialkyl ortho-esters, such as trimethyl orthoformate, triethyl orthoformate, triisopropyl orthoformate or corresponding orthoacetates, to give acyclic acetals of the general formula (VI). Preference is given here to the reactions with ethylene glycol, pyrocatechol, trimethyl orthoformate, triethyl orthoformate or triisopropyl orthoformate.

Chlorobenzaldehydes can be reacted with 1,2-aminoalcohols which are monosubstituted on the nitrogen to give correspondingly substituted oxazolidines of the general formula (VII) by azeotropic distillation of the water of reaction (T. H. Fife, L. Hagopian, J. Am. Chem. Soc. 1968, 1007–1014). Preferred aminoalcohols are N-methyl-2-aminoethanol, N-ethyl-2-aminoethanol, N-propyl-2-aminoethanol, N-butyl-2-aminoethanol, N-phenyl-2-aminoethanol, N-benzyl-2-aminoethanol, N-methyl-2-aminopropanol, N-ethyl-2-aminopropanol, N-propyl-2-aminopropanol, N-butyl-2-aminopropanol, particularly preferably N-ethyl-2-aminoethanol, N-butyl-2-aminoethanol, N-phenyl-2-aminoethanol, N-benzyl-2-amino-ethanol.

It is furthermore possible to react the correspondingly substituted chlorobenzoyl chloride with 1,2-aminoalcohols by a method described in J. Org. Chem. 1988, 53, 345–352, to give oxazolines.

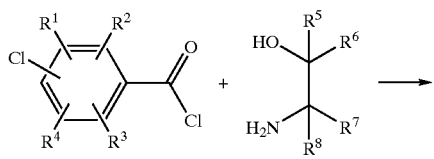

-continued

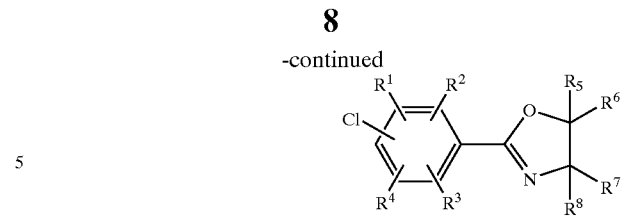

Preference is given here to 2-amino-2-methylpropan-1-ol and 2-aminoethanol.

The compound of the formula (II) is converted in accordance with the invention into the Grignard compound of the formula (III) using Mg powder or turnings in the presence of i) an anthracene compound or ii) an anthracene compound and a transition-metal halide or iii) an anthracene compound and a magnesium halide or iv) an anthracene compound, a transition-metal halide and a magnesium halide or v) a transition-metal halide or vi) a transition-metal halide and a magnesium halide.

The anthracene compounds employed can be unsubstituted anthracene or Mg anthracene, substituted, for example by 1 to 4 ($C_1$–$C_4$)-alkyl groups or phenyl groups, anthracene or Mg anthracene, in particular 9,10-diphenylanthracene or Mg 9,10-diphenylanthracene. The anthracene compounds can be added in amounts of from 0.5 to 100 mol %, preferably from 1 to 10 mol %, based on the haloaromatic compounds, or alternatively formed in situ.

The transition-metal halides are preferably chlorides or bromides, in particular $FeCl_2$, $MnCl_2$, $FeBr_2$ or $MnBr_2$. The transition-metal halides can be added in amounts of from 0.5 to 100 mol %, preferably from 1 to 10 mol %, based on the haloaromatic compounds.

Suitable magnesium halides are $MgCl_2$ and $MgBr_2$. They can be added in amounts of from 0.5 to 100 mol %, preferably from 1 to 10 mol %, based on the haloaromatic compounds.

The Grignard reaction is preferably carried out at the boiling point of the corresponding solvent and under a protective-gas atmosphere. Suitable solvents are usually tetrahydrofuran, diethyl ether, monoglyme and diglyme and a solution of N,N,N',N'-tetramethylethylenediamine in toluene. It may be advantageous before commencement of the reaction to activate the magnesium by a method described in Y.-H. Lai, Synthesis 585–604 (1981) or to carry out the Grignard reaction in the presence of small amounts, for example from 0.01 to 10 mol %, preferably from 0.1 to 1 mol %, based on the haloaromatic compounds, of a haloalkane, such as, for example, 1,2-dibromoethane, bromoethane or iodomethane.

The compound of the formula (III) is novel and is likewise a subject-matter of the present invention. The compound of the formula (III) can be isolated by removing the solvent by distillation under a protective-gas atmosphere.

In order to obtain phenylboronic acids, the compound of the formula (III) is reacted, preferably without interim isolation, with the borate of the formula $B(OR')_3$, in particular with $B(OCH_3)_3$, $B(OEt)_3$ or $B(OiPr)_3$, and subsequently hydrolyzed under aqueous conditions to give a compound of the formula (IV). The reaction with the borate is advantageously carried out at a temperature of from −80° C. to +20° C., preferably from −50° C. to +10° C., in particular from −25° C. to 0° C.

The borate is advantageously employed in a 1- to 1.5-fold molar amount, based on the Grignard compound.

The compound of the formula (IV) can subsequently be hydrolyzed under acidic conditions, for example using sulfuric acid at pH 0 to 3. If D is an acetal or oxazolidine group, a preferred procedure is, when the addition of the borate is complete, to add the reaction mixture to ice-water and to set the pH of the suspension to from 1 to 2, for example using sulfuric acid, giving the compound of the formula (IV) in which $D^1$ is CHO and $Q^1$ and $Q^2$ are each OH.

Oxazolines, i.e. D is a radical of the formula (VIII), can be converted into the aldehyde by a method described in J. Am. Chem. Soc. 1983, 105, 1586–1590, by alkylation on the nitrogen using alkyl halides, for example methyl iodide, methyl bromide, ethyl iodide or ethyl bromide, or using dialkyl sulfates, for example dimethyl sulfate or diethyl sulfate, hydrogenation using complex metal hydrides, such as $LiAlH_4$, $NaBH_4$ or $NaBH_3(CN)$, followed by acidic hydrolysis.

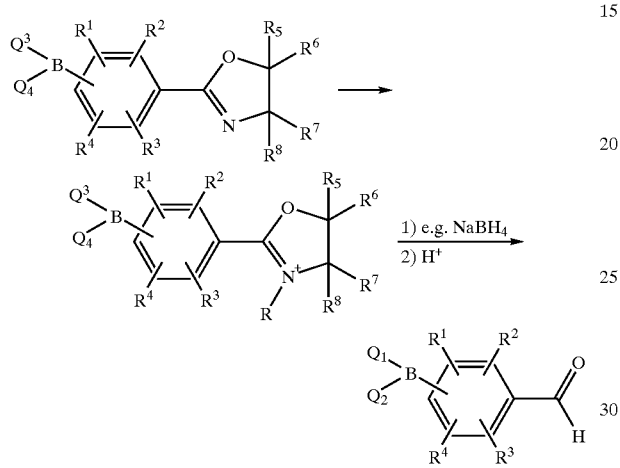

During the hydrolysis, the aldehyde predicting group is removed and the boronate is converted into the free boronic acid. The formylphenylboronic acid of the formula (I) in which Z is CHO can be isolated from the organic phase of the reaction mixture.

Secondary products can be prepared as shown in Scheme 2 by oxidation or reduction of the aldehyde. In this scheme, $Q_{10}$ and $Q_{20}$ are $Q_1$ and $Q_2$, or $Q_3$ and $Q_4$ if the formylphenylboronic acid is esterified, before the oxidation or reduction, by the above-described method using an alcohol on which the radicals $Q_3$ and $Q_4$ are based, in an inert organic solvent. This is particularly advantageous if oxidation is subsequently carried out.

Scheme 2:

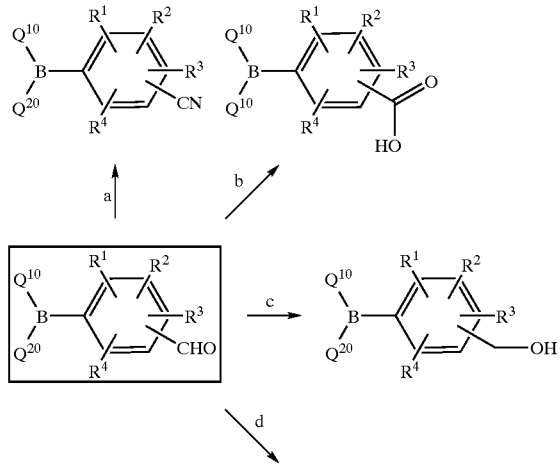

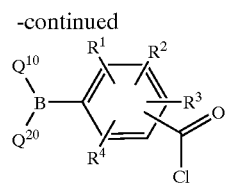

a) From formylphenylboronic acid and its borates, the corresponding cyanophenylboronic acid of the formula (I) in which Z is CN is obtained by reaction with hydroxylamine or hydroxylammonium salts followed by dehydration of the oxime formed. The dehydration can be carried out by heating in glacial acetic acid or in acetic anhydride (J. Chem. Soc. 1933, IX, 43). By a method proposed in EP-A1-0 790 234, the nitrile function is obtained by reaction of the benzaldehyde derivative with hydroxylamine sulfate in the presence of a tertiary amine base and azeotropic distillation of the water of reaction.

b) The corresponding carboxyphenylboronic acid of the formula (I) in which Z is COOH can be prepared by oxidation of formylphenylboronic acid using barium permanganate or potassium permanganate, for example in accordance with U.S. Pat. No. 5,631,364.

c) The compound of the formula (I) in which $Z=CH_2OH$ can be obtained by reduction using Raney nickel/hydrogen or using complex metal hydrides, such as $LiAlH_4$ or $NaBH_4$.

d) The compound of the formula (I) in which Z=COCl can be obtained by a method described in Ginsburg, D., J. Amer. Chem. Soc., 1951, 73, 702–704, by reaction of formylphenylboronic acid with t-BuOCl in carbon tetrachloride.

Starting from cyanophenylboronic acid or borates, further secondary products can be prepared in accordance with Scheme 3.

EXAMPLES

Scheme 3:

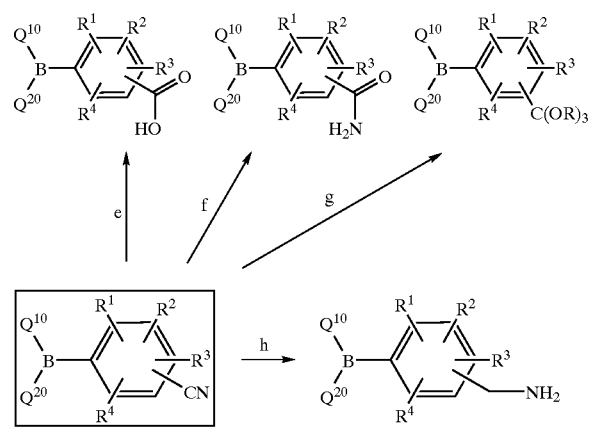

e) Carboxyphenylboronic acids can be obtained by hydrolysis of cyanophenylboronic acid, for example analogously to M. V. Sargent, J. Chem. Soc. Perkin Trans. 1, 1987 (1), 231.

f) Carboxamidophenylboronic acids can be prepared by a method described in Liu, K.-T.; et al., Synthesis 1988 (9), 715, starting from cyanophenylboronic acid using $MnO_2$ on silica gel and water in an organic solvent.

g) Carboxylic acid orthoester phenylboronic acids can be prepared by a method described in P. Hamann et al., Synthetic Commun. (1989) 19 (9–10), 1509–1518, from cyanophenylboronic acid using the corresponding alcohol ROH with addition of anhydrous hydrogen chloride to give the corresponding orthoester, in which R can be $C_1$–$C_{12}$-alkyl or aryl, preferably methyl, ethyl or phenyl.

h) Methyleneaminophenylboronic acids can be prepared by a method described in B. S. Biggs et al., Org. Synth. 1947, 27, by hydrogenation using hydrogen and Raney nickel as catalyst.

Example 1

2.7 g (110 mmol) of magnesium turnings were added to a solution of 2 g (11 mmol) of anthracene in 100 ml of THF, and a few drops of 1,2-dibromoethane were added. After the mixture had been stirred at room temperature for about 2 hours, the bright orange precipitate of magnesium anthracene had formed. A solution of 19 g (100 mmol) of 4-chlorobenzaldehyde dimethyl acetal in 100 ml of THF was added to the refluxing suspension over the course of 1 hour. After the mixture had refluxed for 4 hours, the yield of Mg 4-chlorobenzaldehyde dimethyl acetal according to GC analysis (determined as benzaldehyde after hydrolysis using dilute HCl) was 90%.

Example 2

100 ml of THF, 1.18 g (5.5 mmol) of anhydrous iron(II) bromide, 1.01 g (5.5 mmol) of magnesium bromide and a few drops of dibromoethane were added to 2.7 g (110 mmol) of magnesium turnings. After the mixture had been stirred at room temperature for about 2 hours, the mixture had become a dark-brown to black color. A solution of 19 g (100 mmol) of 4-chlorobenzaldehyde dimethyl acetal in 100 ml of THF was added to the refluxing suspension over the course of 1 hour. After the mixture had refluxed for 4 hours, the yield of Mg 4-chlorobenzaldehyde dimethyl acetal according to GC analysis (determined as benzaldehyde after hydrolysis using dilute HCl) was 95%.

Example 3

4-Formylboronic Acid

A Grignard solution as obtained from Example 1 or 2 was added dropwise at −50° C. to a suspension of 10.4 g (100 mmol) of trimethyl borate in 300 ml of THF over the course of 3 hours. When the addition was complete, the white suspension was poured into 200 g of ice-water. The suspension was adjusted to pH 1 to 2 using conc. $H_2SO_4$. When the hydrolysis was complete, the phases were separated, giving 12.45 g (83 mmol) of 4-formylboronic acid.

Example 4

Example 3 was repeated with a reaction temperature of −15° C.: yield 11.85 g (79 mmol) of 4-formylboronic acid.

Example 5

4-(4,4,5,5-Tetramethyl[1,3,2]dioxaborolan-2-yl) benzaldehyde

A suspension of 5 g (33.3 mmol) of 4-formylphenylboronic acid and 3.93 g (33.3 mmol) of pinacol in 25 ml of toluene was refluxed on a water separator. When all the water of reaction had been removed, a clarifying filtration was carried out, and the solvent was removed by distillation until the product started to crystallize, giving 7.2 g (31 mmol) of product.

Example 6

4-Cyanophenylboronic Acid 17 g (100 mmol) of hydroxylamine sulfate were added at 70° C. to 15 g (100 mmol) of 4-formylphenylboronic acid, 10 g of water, 5 g (60 mmol) of pyridine and 200 ml of toluene. The mixture was then refluxed on a water separator. When all the water had been removed, the pyridinium salts were separated off, giving 12.7 g (87%) of 4-cyanophenylboronic acid.

Example 7

Pinacolyl 4-Cyanophenylboronate 17 g (100 mmol) of hydroxylamine sulfate were added at 70° C. to 23.2 g (100 mmol) of pinacolyl 4-formylphenylboronate, 10 g of water, 5 g (60 mmol) of pyridine and 200 ml of toluene. The mixture was then refluxed on a water separator. When all the water had been removed, the pyridinium salts were separated off, giving 20.8 g (91%) of pinacolyl 4-cyanophenylboronate.

Example 8

4-Carboxyphenylboronic Acid 14.5 g (100 mmol) of 4-cyanophenylboronic acid were dissolved in a mixture of 11 g (200 mmol) of potassium hydroxide and 10 g of water in 100 ml of methanol, and the mixture was refluxed until the evolution of ammonia gas was complete, giving 14.9 g (90 mmol) of 4-carboxyphenylboronic acid.

Example 9

Esterification of 4-Carboxyphenylboronic Acid

4-Carboxyphenylboronic acid and an equimolar amount of the appropriate diol shown in Table 1 were refluxed in 200 ml of toluene. When all the water formed had been removed on a water separator (after about 1 hour), the solution was filtered through a suction filter while still hot. The solvent was subsequently removed by distillation.

TABLE 1

| Diol | Amount of starting material | Product | Yield |
| --- | --- | --- | --- |
| Pinacol | 30 g (180 mmol) | 4-(4,4,5,5-Tetramethyl-[1,3,2]dioxaborolan-2-yl)-benzoic acid | 43.1 g (97%) |
| Neopentyl glycol | 16.6 g (100 mmol) | 4-(5,5-Dimethyl-[1,3,2]dioxaborinan-2-yl)-benzoic acid | 22 g (94%) |
| Ethylene glycol | 200 g (1.2 mol) | 4-[1,3,2]Dioxaborolan-2-yl-benzoic acid | 227.1 g (98%) |
| Diethanolamine | 20 g (120 mmol) | 4-[1,3,6,2]Dioxazaborocan-2-yl-benzoic acid | 27.5 g (98%) |

Example 10

4-Carboxamidophenylboronic Acid 10 g (68 mmol) of 4-cyanophenylboronic acid were refluxed for 6 hours in a mixture of 12 g (135 mmol) of manganese dioxide, 10 g of water and 150 ml of cyclohexane. 9.6 g (58 mmol) of 4-carboxamidophenylboronic acid were isolated.

Example 11

4-(Trimethoxymethyl)phenylboronic Acid 30 g (203 mmol) of 4-cyanophenylboronic acid were dissolved in 200 ml of methanol, and 200 ml of 1 M hydrogen chloride solution in diethyl ether were added. The reaction mixture was refluxed for 8 hours, giving 38.5 g (170 mmol) 4-(trimethoxymethyl)phenylboronic acid

Example 12

4-(Methylamino)phenylboronic Acid 30 g (203 mmol) of 4-cyanophenylboronic acid were dissolved in 200 ml of tetrahydrofuran, and 0.5 g of Raney nickel were added. A stream of hydrogen was passed through the reaction mixture for 8 hours, giving 29.8 g (199 mmol) of 4-(methylamino)phenylboronic acid.

Example 13

4-(Hydroxymethyl)phenylboronic Acid 15 g (100 mmol) of 4-formylphenylboronic acid were dissolved in 200 ml of tetrahydrofuran, and 0.25 g of Raney nickel were added. A stream of hydrogen was passed through the reaction mixture for 8 hours, giving 14.8 g (97 mmol) of 4-(hydroxymethyl)phenylboronic acid.

Example 14

Pinacolyl 4-(Hydroxymethyl)phenylboronate

Analogously to Example 12, 12 g (52 mmol) of pinacolyl 4-formylphenylboronate were hydrogenated in 100 ml of methanol, giving 11.7 g (50 mmol) of 4-(hydroxymethyl) phenylboronic acid.

What is claimed is:
1. A process for the preparation of a compound of the formula (I)

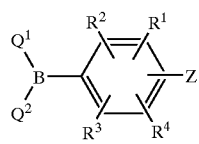

(I)

in which $Q^1$ and $Q^2$ are each OH or together are a divalent radical of the formula (Ib)

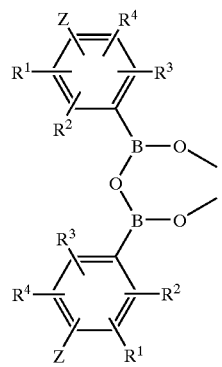

(Ib)

Z is —CHO, D, —CH$_2$Y or X, where D is a protected aldehyde group, Y is hydroxyl or amino, and X is cyano, COOH, COCl, CONH$_2$ or C(OR)$_3$, where R is $C_1$–$C_5$-alkyl or phenyl, and where Z is in the ortho-, meta- or para-position to the boronic acid radical;

$R^1$ to $R^4$, independently of one another, are hydrogen, $C_1$–$C_{12}$-alkyl, $C_2$–$C_{12}$-alkenyl, $C_2$–$C_{12}$-alkynyl, $C_3$–$C_{12}$-cycloalkyl, ($C_1$–$C_{12}$-alkoxy, O-phenyl, O-benzyl, aryl, heteroaryl, fluorine, N(alkyl)$_2$, N[Si($C_1$–$C_4$-alkyl)$_3$]$_2$ or CF$_3$, or $R^1$ and $R^2$, or $R^3$ and $R^4$, or $R^1$ and $R^2$, and $R^3$ and $R^4$ together form a 5- or 6-membered aliphatic or aromatic ring; said process comprising the steps of:

a) reacting a compound of the formula (II)

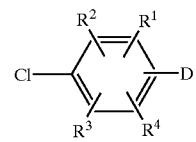

(II)

with magnesium in the presence of
  i) an anthracene compound and, optionally a transition-metal halide and, optionally, a magnesium halide; or
  ii) a transition-metal halide and, optionally, a magnesium halide,
where the anthracene compound is a compound from the group consisting of anthracene, Mg anthracene, substituted anthracene and substituted Mg anthracene, to give an arylmagnesium chloride of the formula (III)

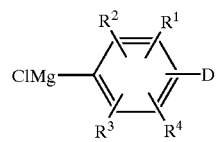

(III)

b) reacting the compound of the formula (III) with a borate of the formula B(OR')$_3$, in which R' are identical to or different from one another and are straight-chain or branched ($C_1$–$C_8$)-alkyl radicals, phenyl radicals which are unsubstituted or substituted by one or two ($C_1$–$C_4$)-alkyl groups or ($C_1$–$C_4$)-alkoxy groups, and hydrolyzing the product to give a compound of the formula (IV)

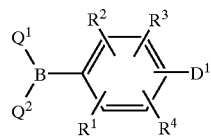

(IV)

in which
D¹ is CHO or D;
Q¹ and Q² are each OH or together are a divalent radical of the formula (IVb)

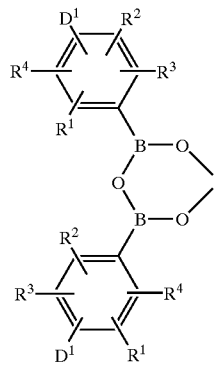

(IVb)

c) optionally oxidizing the compound of the formula (IV) or (IVb) in which D¹ is CHO to give a compound of the formula (I) In which Z is X, or optionally reducing the compound of the formula (IV) or (IVb) to give a compound of the formula (I) in which Z is CH₂Y.

2. The process as claimed in claim 1, wherein $R^1$ to $R^4$ are hydrogen, methyl, ethyl, propyl, butyl, methoxy, ethoxy, propoxy, butoxy or fluorine.

3. The process as claimed in claim 1, wherein D is an acetal of the formula (V) or (VI)

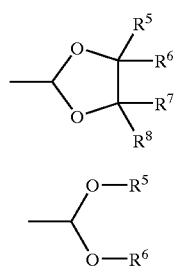

(V)

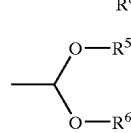

(VI)

in which $R^5$ to $R^8$ are identical or different and are hydrogen, $C_1$–$C_{12}$-alkyl or phenyl, or $R^6$ and $R^7$ together form a 5- or 6-membered aliphatic or aromatic ring; or D is an oxazolidine of the formula (VII) or an oxazoline of the formula (VIII)

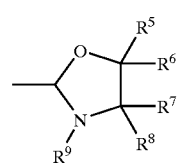

(VII)

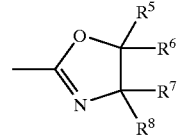

(VIII)

in which $R^9$ is $C_1$–$C_6$-alkyl, phenyl or benzyl, unsubstituted or substituted on the aromatic ring.

4. The process as claimed in claim 1, wherein the borate B (OR¹)₃ is trimethyl borate, tiethyl borate, tri-n-propyl borate, trisopropyl borate, tri-n-butyl borate or triisobutyl borate.

5. The process as claimed in claim 1, wherein step a) is carried out in the presence of anthracene, Mg anthracene, 9,10-diphenylanthracene or Mg 9,10-diphenylanthracene.

6. The process as claimed in claim 1, wherein step aI is Carried out in the presence of $MgCl_2$ or $MgBr_2$, and in the presence of $FeCl_2$, $MnCl_2$, $FeBr_2$ or $MnBr_2$.

7. The process as claimed in claim 1, wherein the compound of the formula (IV) is esterified using an alcohol of the formula HO-($C_1$–$C_{12}$)-alkyl, HO-($C_2$–$C_{12}$)-alkenyl, HO-($C_2$–$C_{12}$)-alkynyl, HO-aryl, HO-alkylaryl, ($C_3$–$C_{12}$)-cycloalkane-1,2-diol, cycloalkane-1,2-diol, ($C_5$–$C_{12}$)-cycloalkene-1,2-diol, ($C_5$–$C_{12}$)-cycloalkane-1,3-diol, ($C_5$–$C_{12}$)-cycloalkene-1,3-diol or using an alcohol of the formulae (1) to (6)

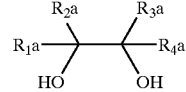

(1)

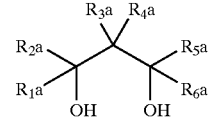

(2)

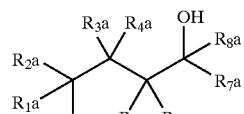

(3)

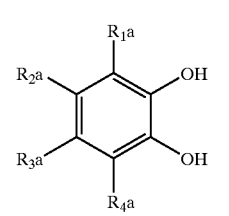

(4)

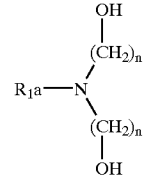

(5)

-continued (6)

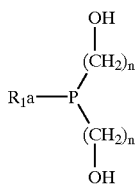

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, ($C_1$–$C_{12}$)-alkoxy, O-phenyl, O-benzyl, aryl, heteroaryl, fluorine, chlorine, $NH_2$, NH(alkyl), N(alkyl)$_2$, $N[Si(C_1$–$C_4$-alkyl)$_3]_2$ or $CF_3$, two adjacent radicals $R_1a$ to $R_8a$ together optionally form a 5- or 6-membered aliphatic or aromatic ring, and in which n is an integer from 2 to 12.

8. The process as claimed in claim 1, wherein the compound of the formula (I) is esterified using an alcohol of the formula HO-($C_1$–$C_{12}$)-alkyl, HO-($C_2$–$C_{12}$)-alkenyl, HO-($C_2$–$C_{12}$)-alkynyl, HO-aryl, HO-alkylaryl, ($C_3$–$C_{12}$)-cycloalkane-1,2-diol, cycloalkane-1,2-diol, ($C_5$–$C_{12}$)-cycloalkene-1,2-diol, ($C_5$–$C_{12}$)-cycloalkane-1,3-diol, ($C_5$–$C_{12}$)-cycloalkene-1,3-diol or using an alcohol of the formulae (1) to (6)

(1)

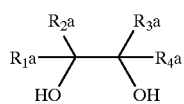

(2)

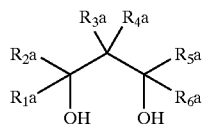

(3)

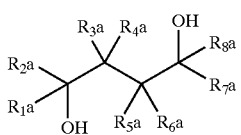

(4)

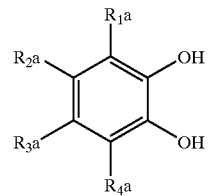

(5)

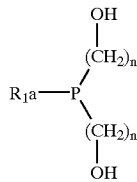

(6)

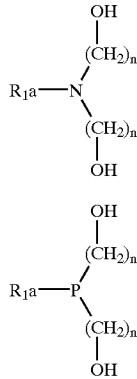

in which $R_1a$ to $R_8a$, independently of one another, are hydrogen, $C_1$–$C_{12}$-alkyl, $C_1$–$C_{12}$-hydroxyalkyl, $C_2$–$C_{12}$-alkenyl, $C_2$–$C_{12}$-alkynyl, $C_3$–$C_{12}$-cycloalkyl, ($C_1$–$C_{12}$)-alkoxy, O-phenyl, O-benzyl, aryl, heteroaryl, fluorine, chlorine, $NH_2$, NH(alkyl), N(alkyl)$_2$, $N[Si(C_1$–$C_4$-alkyl)$_3]_2$ or $CF_3$, two adjacent radicals $R_1a$ to $R_8a$ together optionally form a 5- or 6-membered aliphatic or aromatic ring, and in which n is an integer from 2 to 12.

9. The process as claimed in claim 7, wherein, after the esterification, the aldehyde group is oxidized to the carboxyl, nitrile or carbonyl chloride group.

10. The process as claimed in claim 7, wherein, after the esterification, the aldehyde group is reduced to the methylamino or hydroxymethyl group.

* * * * *